United States Patent [19]
Sessions

[11] Patent Number: 4,516,581
[45] Date of Patent: May 14, 1985

[54] EKG ELECTRODE

[75] Inventor: Robert W. Sessions, Burr Ridge, Ill.

[73] Assignee: Ferris Manufacturing Corp., Burr Ridge, Ill.

[21] Appl. No.: 506,043

[22] Filed: Jun. 20, 1983

[51] Int. Cl.³ .................................................. A61B 5/04
[52] U.S. Cl. ...................................... 128/639; 128/641
[58] Field of Search .............................. 128/639–641, 128/643, 644, 783, 798, 802, 803

[56] References Cited
U.S. PATENT DOCUMENTS 3,610,229 10/1971 Zenkich ........................... 128/641
3,868,946 3/1975 Hurley ............................. 128/641
4,088,133 5/1978 Twentier ......................... 128/644
4,391,279 7/1983 Stein ............................... 128/643
4,441,501 4/1984 Parent ............................. 128/641

Primary Examiner—Lee S. Cohen
Attorney, Agent, or Firm—Winburn & Gray, Ltd.

[57] ABSTRACT

An EKG electrode is disclosed including a conductive ring positioned around a jelled foam member which is positioned against a surface of a metal contact. The ring may be formed of a conductive medical grade plastic or may be formed by plating a non-conductive ring with a conducting metal.

7 Claims, 7 Drawing Figures

EKG ELECTRODE

BACKGROUND OF THE INVENTION

1. Field of the Invention:

The invention pertains to improvements in EKG electrodes.

2. Prior Art:

EKG electrodes are well known. Several variations are shown in continuation-in-part U.S. patent application Ser. No. 247,560, filed Mar. 25, 1981, of Sessions et al, now U.S. Pat. No. 4,441,500.

SUMMARY OF THE INVENTION

An improvement to EKG electrodes wherein a conductive ring is positioned around a jell impregnated foam cylinder usually formed on such electrodes. The ring is conductive being either a medical grade flexible carbon composition or a rigid plastic plated with a conducting metal such as silver. The ring provides the primary body contact.

DESCRIPTION OF THE PREFERRED EMBODIMENTS

Not by way of limitation, but by way of disclosing the best mode of practicing my invention, and by way of enabling one of skill in the art to practice my invention, FIGS. 2 to 6 disclose two embodiments of my invention.

Figure 1:
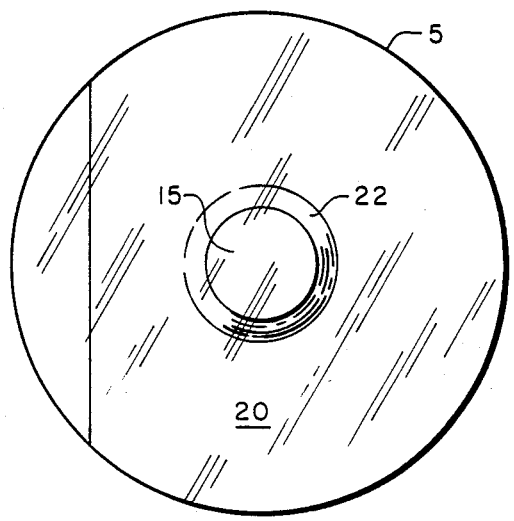
FIG. 1 is a planar top view of a prior art electrode.

FIG. 1 discloses prior art EKG electrodes of a type shown in continuation-in-part U.S. patent application, Ser. No. 247,560. A body portion 5 has attached thereto a conducting contact 10 which extends through said body portion 5 to be in contact with a jell impregnated foam member 15. When the member 5 is affixed to a body B, as in FIG. 4, the jell impregnated member is in contact with the surface of the body B. A cover 20 protects and seals the electrode before use.

Figure 2:
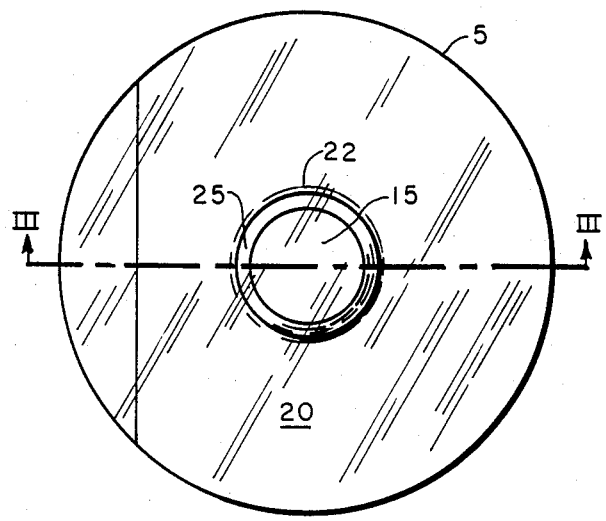
FIG. 2 is a planar top view of the improved EKG electrode according to this invention.
Figure 3:
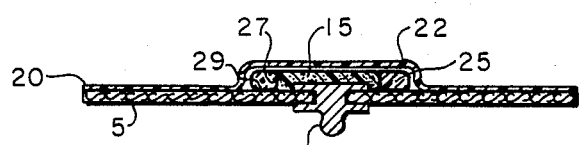
FIG. 3 is a sectional view taken along the line III—III of FIG. 2.
Figure 4:
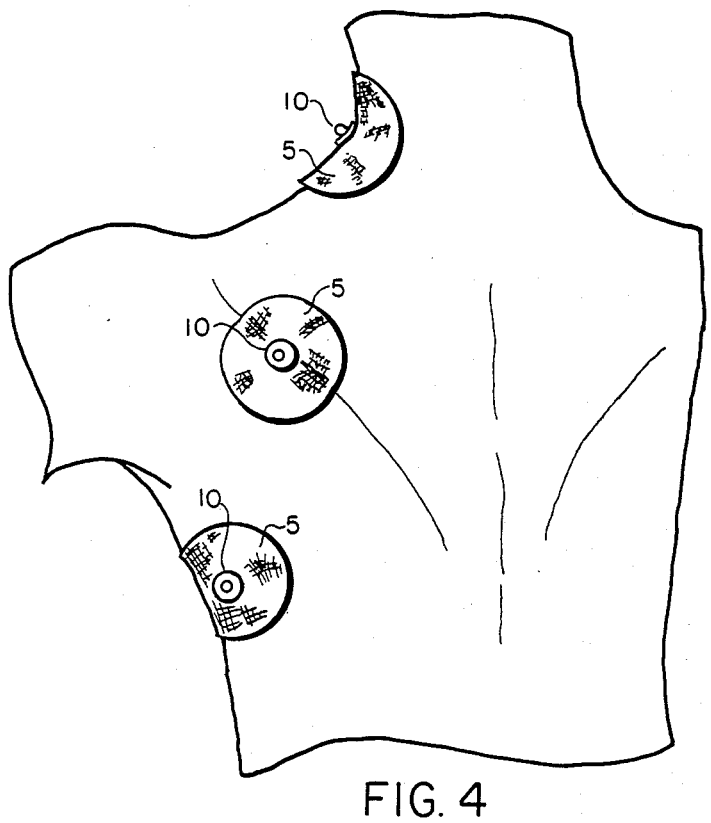
FIG. 4 is a rear view of a body B with several EKG electrodes attached thereto.

In my improved EKG electrode FIGS. 2, 3, an annular conducting ring 25 is placed around the cylindrical jell impregnated foam member 15. The ring 25 can be a medical grade flexible plastic including 50% carbon. The ring 25 can be latex or some other rubber including carbon or any other material that will make it conductive. The primary contact to the body with my improved electrode is through the ring 25. The cylindrical, jell impregnated foam member 15 serves to make an electrical connection between the ring 25 and electrical contact 10.

The flexible conductive ring 25 improves the electrical signal measurable at electrode 10 off of body B because it provides a larger conductive area in contact with the surface of the body B than is obtainable without the ring 25. Further, ring 25 eliminates what is known as "artifact", movement of the electrode with respect to the skin of the body B with a resultant deterioration in the quality of the electric circuit.

As can be seen in FIG. 3, ring 25 is in physical and electrical contact with a peripheral surface 27 of the cylinder 15 and in physical contact with a part 29 of the surface of the body portion 5. I have found that rings with an inner radius of $\frac{5}{8}''$ to $\frac{3}{4}''$ are of a suitable size. Rings 1/16" to $\frac{1}{8}''$ thick are also of a suitable size. The objective of using ring 25 is to increase the electrical area in contact with the body. The jell which is conducting acts to maintain contact 10 at the same electrical potential as ring 25.

While the embodiment of FIG. 3 shows the ring 25 in physical contact with member 15 at the surface 27, in another form of my invention the member 15 would not necessarily be in physical contact with member 25. Rather, The electrical connection between ring 25 and member 15 can be made using any commercially available conducting jell in contact with the ring 25 and member 15. What is required in my improvement is that the contact member 10 be at the same body electrical potential as the ring 25.

Figure 5:
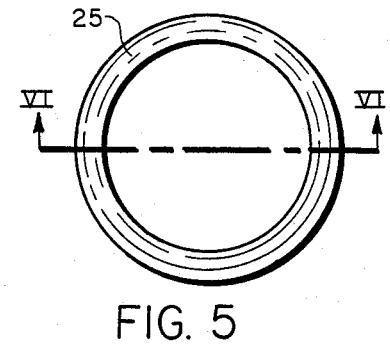
FIG. 5 is a plan view from the top of a conducting ring.
Figure 6A:
FIG. 6A is a sectional view taken along the line VI—VI of FIG. 5 showing a flexible carbon composition ring.
Figure 6B:
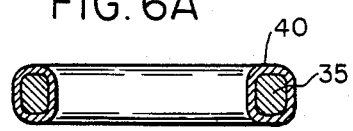
FIG. 6B is a sectional view taken along the line VI—VI showing an alternate rigid plated plastic ring.

FIG. 5 is a view of ring 25 removed from the electrode. Two alternate embodiments to ring 25 are shown in FIGS. 6A, 6B. FIG. 6A is a flexible carbon composition ring that is conductive. FIG. 6B is a rigid ring 35 with a conductive layer 40 preferably silver. Nickel could also be used as an alternate to silver. While the rigid ring 35 has the layer 40 to make it conductive, any other means to make it conductive could also be used.

It will be apparent to those skilled in this art that various minor modifications may be made without departing from the spirit and scope of the novel concepts of the present invention.

I claim as my invention:

1. In an EKG electrode with a body portion to which is attached a conducting contact member in electrical contact with a jell impregnated foam member, an improvement comprising:

means for surrounding said foam member positioned so as to be in physical contact with a part of said body portion as well as in electrical contact with said foam member, and wherein;

said means surrounding comprises a conductive annular ring formed of a selected medical grade plastic.

2. The improved EKG electrode in accordance with claim 1 wherein said annular ring is flexible.

3. The improved EKG electrode in accordance with claim 1 wherein said annular ring is plated with a selected conducting metal.

4. The improved EKG electrode in accordance with claim 1 wherein said annular ring includes a selected quantity of carbon so as to be conductive and wherein said annular ring is flexible.

5. In an EKG electrode with a body portion to which is attached a conducting electrode in contact with a jell impregnated foam member, an improvement comprising:

an annular ring positioned so as to surround and be in electrical contact with said jell impregnated foam member and so as to be in physical contact with a part of said body portion and wherein said annular ring is formed of a flexible plastic containing a selected amount of carbon so as to be conductive.

6. In an EKG electrode with a body portion to which is attached a conducting electrode in contact with a jell impregnated foam member an improvement comprising:

an annular ring positioned so as to surround and be in electrical contact with said jell impregnated foam member and so as to be in contact with a part of said body portion, and wherein said annular ring is formed of a rigid plastic which has been plated with a selected conducting metal.

7. The improved EKG electrode according to claim 6 wherein said annular ring is plated with silver.

* * * * *